United States Patent [19]

Convers

[11] 4,414,136

[45] Nov. 8, 1983

[54] CATALYSTS FOR ETHYLENE OXYCHLORINATION

[75] Inventor: Ronald J. Convers, Ponca City, Okla.

[73] Assignee: Conoco Inc., Ponca City, Okla.

[21] Appl. No.: 364,957

[22] Filed: Apr. 2, 1982

[51] Int. Cl.$^3$ .............................................. B01J 27/10
[52] U.S. Cl. .................................. 502/225; 570/243; 570/245; 502/231
[58] Field of Search ................. 252/441; 570/243, 245

[56] References Cited

U.S. PATENT DOCUMENTS

| | | | |
|---|---|---|---|
| 3,468,968 | 9/1969 | Baker et al. | 570/243 |
| 3,527,819 | 9/1970 | Berkowitz et al. | 252/441 X |
| 3,634,330 | 1/1972 | Michel et al. | 252/441 |
| 4,323,716 | 4/1982 | Canavesi et al. | 252/441 X |

Primary Examiner—Patrick Garvin
Attorney, Agent, or Firm—Cortlan R. Schupbach, Jr.

[57] ABSTRACT

Highly active, improved ethylene oxychlorination catalysts are prepared by forming alumina having specific pore volume characteristics and impregnating such alumina with an oxychlorination catalyst such as $CuCl_2$. The improved catalysts of the present invention utilize an alumina carrier having a pore volume distribution such that substantially no pores are present which have diameters of less than 150 Ångstroms and the total alumina carrier has a surface area of at least 30 square meters per gram.

5 Claims, 6 Drawing Figures

CATALYSTS FOR ETHYLENE OXYCHLORINATION

This invention relates to an improved ethylene oxychlorination catalyst. More specifically, this invention relates to an improved ethylene oxychlorination catalyst having specific pore volume distributions in order to provide an active catalyst yielding increased ethylene dichloride product at the expense of by-products.

The production of chlorinated hydrocarbons and more particularly the oxychlorination process comprising an unsaturated hydrocarbon in a mixture of hydrogen chloride and oxygen are known conventionally as oxychlorination reactions. It is likewise well known that the oxychlorination of hydrocarbons generally occurs in the gaseous phase at an elevated temperature, the temperature depending on whether or not the hydrocarbon to be chlorinated is saturated. When it is desired to oxychlorinate unsaturated hydrocarbons, temperatures of around 250°–300° C. are normally used. These temperatures, however, are desirably as low as possible in order to avoid volatilization of the metallic halides of the catalysts with subsequent deactivation and moreover to avoid the secondary formation of substitution products which are troublesome in the desired product stream.

Various methods have been attempted to reduce these undesirable influences upon the chlorinated addition products. First, lowering the reaction temperature has been attempted, but the subsequent lowering of production obtained and the shift in product distribution has been undesirable. Likewise, it has been attempted to support the metallic chloride catalysts on porous supports such as diatomaceous earth, silica or activated alumina, wherein the alumina has undergone treatment temperatures of at least 405° C., commonly known as calcining.

However, when alumina carriers are used, especially at temperatures in excess of 300° C., these catalysts have not been sufficiently selective to avoid undesirable side reactions, such as substitution reactions associated with the higher reaction temperature.

In order to avoid these problems, the art has generally used reaction temperatures in the range of 240° C. to 280° C. to avoid side reactions and has utilized alumina having extremely large amounts of very small pores at or below 100 Ångstroms in size in order to facilitate reaction. These reactions are extremely rapid and prevent the loss of valuable catalytic metals through vaporization.

However, these reactions, while generally effective and in common use today, likewise yield large amounts of troublesome by-products such as chloral and ethyl chloride which are difficult to separate and difficult to dispose. These problems are known in the prior art. Attempts have previously been known to solve such problems through the use of process modifications as described in U.S. Pat. No. 3,454,663. Likewise, the addition of water or steam to oxychlorination reactors has been shown in British Pat. No. 932,130, British Pat. No. 1,117,694; U.S. Pat. No. 3,444,252 and U.S. Pat. No. 4,113,786.

Spanish Pat. No. 396,446 teaches that alumina as well as silica gel, pumice stone, diatomaceous earth and the like can be used for supporting the active metallic chlorides for oxychlorination reactions. German patent application No. 2,651,974 teaches cupric chloride materials distributed on aluminum oxide comprising eta aluminum oxide, theta aluminum oxide, kappa aluminum oxide, delta aluminum oxide, chi aluminum oxide, or mixtures of these. This catalyst has a specific surface in the range of 40 to 120 square meters per gram.

U.S. Pat. Nos. 3,979,504 and 3,773,691 both teach similar catalysts wherein an alumina carrier has surface areas of 275 to 400 squares meters per gram for a very active catalyst. U.S. Pat. Nos. 4,098,874 and 3,202,4880 show similar catalysts having alumina carriers with diatomaceous earth supports having surface areas of 100 to about 300 square meters per gram. U.S. Pat. No. 4,098,874 shows pore diameter ranges of from about 20 to about 80 Ångstroms as being most preferred.

However, the drawbacks of the prior art are all inherent in the catalysts described in these references. It would therefore be of great benefit to provide a catalyst for the oxychlorination of hydrocarbons which provides more product EDC at the expense of by-products and has a long catalyst life while providing high activity.

It is therefore an object of the present invention to provide an improved oxychlorination catalyst. Other objects will become apparent to those skilled in this art as the description proceeds.

We have now discovered that surprisingly improved ethylene oxychlorination catalysts can be obtained by slightly lowering the rate of reaction by using conventional copper chlorides or mixtures of copper chlorides with a Group I or II metal chloride such as potassium chloride, when the alumina carrier has substantially no pores less than 150 Ångstroms in diameter and a surface area of at least 30 square meters per gram.

The effectiveness of these catalysts is distinctly surprising in view of the teachings of the prior art that extremely small catalyst pores are preferred in order to increase the reaction rate and allow lower reaction temperatures. However, in the present invention these extremely active small pores are purposely omitted from the carrier. This lack of small pores may retard the reaction to a slight degree, which is necessary to produce ethylene dichloride (EDC) in higher concentrations at the expense of troublesome by-products such as chloral or ethyl chloride.

The alumina carriers of the present invention can be prepared by (a) forming the alumina into the desired shape, then (b) placing the alumina above liquid water in a closed vessel and heating for from about 2 to about 10 hours at a temperature of from about 150° C. to about 550° C. while allowing pressure to reach autogeneous levels, then (c) recovering the alumina and calcining the recovered alumina for a period of time ranging from about 15 minutes to about 10 hours at a temperature ranging from about 450° C. to about 1000° C.

The alumina carrier of the present invention can be derived from any source, either natural or synthetic and can contain any by-products not detrimental to the oxychlorination reaction, all of which is known in the art. The critical aspect of the present invention is that the alumina support contains substantially no pores having an Ångstrom size of less than 150 as determined by the method of the mercury porisometer.

Preferably, the alumina of the present invention will have a peak in the pore volume distribution between 150 Ångstroms and 250 Ångstroms such that a majority of the active pores lie in this range.

Preferably, but not critically, the alumina carrier of the present invention is a bimodal alumina having two pore size distributions, one in the range of 150 Angstroms to 250 Angstroms, and a second, much higher peaked pore size wherein the pore size ranges between about 10,000 Angstroms and about 120,000 Angstroms. However, it is emphasized that when using aluminas wherein the pore size distribution in the range of 150 to 250 with an average surface area of 30 square meters per gram or larger, the majority of the advantages of the present invention will be obtained.

Alumina carriers have previously been prepared in the presence of water. Representative but non-exhaustive examples of such art are U.S. Pat. No. 3,202,480 which shows preparation of alumina spheres by aging in hot water or steam followed by calcination. Steam treatment of alumina supports followed by calcination is disclosed in U.S. Pat. No. 3,974,100. Aging alumina with water in a closed container at high temperature is shown in U.S. Pat. No. 3,264,069. Treatment of shaped alumina by steam is shown in U.S. Pat. No. 2,887,455. However, in none of these prior art references is any elimination of the small pore sizes critical to the process of the present invention shown, nor is the use of such materials disclosed to be an advantage in the oxychlorination of hydrocarbons.

The term "substantially no pores below 150 Angstroms" as used in the instant specification and claims is intended to describe the substantial lack of such pores. Those skilled in this art will realize that it is almost impossible to prepare an alumina having absolutely no pores in this size range, but using the process of the present invention it is possible to substantially eliminate such pores. In sum total, the total differential pore volume as described in cubic centimeters per gram of the pore diameters of 150 Angstroms and below should not exceed 0.050 cc/g and of course alumina carriers having absolutely no pore content in this range are desired.

The improved process of the present invention proceeds primarily by producing ethylene dichloride at the expense of ethyl chloride. Ethyl chloride is a significant by-product in commercial ethylene oxychlorination reactions. In the present invention we have found that ethyl chloride is made at the direct expense of ethylene dichloride, i.e. if ethyl chloride were not made the corresponding feed materials would be incorporated essentially all into ethylene dichloride, providing a two-fold benefit in that ethyl chloride is reduced in concentration as a by-product and the desired material (EDC) is made directly at the expense of the non-desired by-product.

In addition, we have found that a critical chemical property of copper chloride based ethylene oxychlorination catalysts lies in the mole ratio of $Cu^{+2}$ to basic materials such as Group I or Group II metal salts on the catalyst surface. Representative examples of these materials are potassium chloride, lithium chloride, magnesium chloride, sodium chloride, and, if desired, the bromides of these metals. Under a given set of pressure, temperature and reactants, the mole ratio of basic salts to $Cu^{+2}$ is related inversely linearly with ethyl chloride selectivity. This effect has been previously reported, as for example in U.S. Pat. Nos. 4,123,467 and 4,206,180, assigned to Stauffer Chemical Company. However, this effect has previously been of limited value to commercial operations since the basic salts act as oxychlorination catalyst poisons and long term catalyst activity is diminished. For this reason, basic catalyst supports, as represented by magnesium oxide, yield less active oxychlorination catalysts. In the present invention, the ratio of active catalyst ($CuCl_2$) to catalyst retarder (KCl in these examples) can be substantially increased without coking, spalling, vaporization and the like experience with prior art catalysts.

Under a given set of operating conditions and with a given mole ratio of $Cu^{+2}$ to basic salts, ethyl chloride selectivity tends to increase with temperature when utilizing alumina based oxychlorination catalyst. However, the ethyl chloride selectivity (inversely, selectivity to ethylene dichloride) is also critically dependent on the pore volume distribution of the oxy catalyst carrier. Selectivity of the oxychlorination reaction over catalysts on alumina carriers to ethyl chloride can be reduced to on the order of 10 to 15% of amounts seen with commercial catalysts by utilizing the catalysts of the present invention. One surprising benefit of the present invention is that when utilizing the catalyst carriers of the present invention, selectivity to ethyl chloride by-product becomes essentially insensitive to hot spot temperature over a broad range of about 260° C. to about 360° C., allowing the use of increased temperatures and faster reaction times if desired.

Critical pore volume distribution of the present invention occurs entirely within the catalyst micropore range of about 800 Angstroms or less, where most oxychlorination reaction occurs. According to the present invention, we have discovered an inverse linear relationship between ethyl chloride selectivity and the sum of the fractions differential pore volume all over corresponding micropore diameters as determined for a catalyst by standard mercury porosimetry techniques. The pore volume in this specification and claims were determined using mercury penetration techniques with pressures up to 50,000 pounds per square inch gauge (psig) using a mercury porosimeter Model 905-1, manufactured by Micrometrics Corporation of Norcross, Georgia USA.

The basis of the present invention resides in the discovery that about 80 to 90% of the ethyl chloride produced with conventional copper chloride based fixed bed oxychlorination catalysts is produced in catalyst micropores of less than 150 Angstroms pore diameter as measured by porosimetry techniques. Ethyl chloride selectivity decreases markedly as the differential pore volume corresponding to smaller diameter micropores decreases. This effect is graphically illustrated in FIG. 1, wherein tests were actually carried out using a pressure of 124.7 pounds per square inch actual (psia), utilizing various alumina supports having different pore volume characteristics, and the results extrapolated to the same (0.17) $K^+:Cu^{++}$ mole ratio and to the same hot-spot temperature (300° C.).

Figure 1:
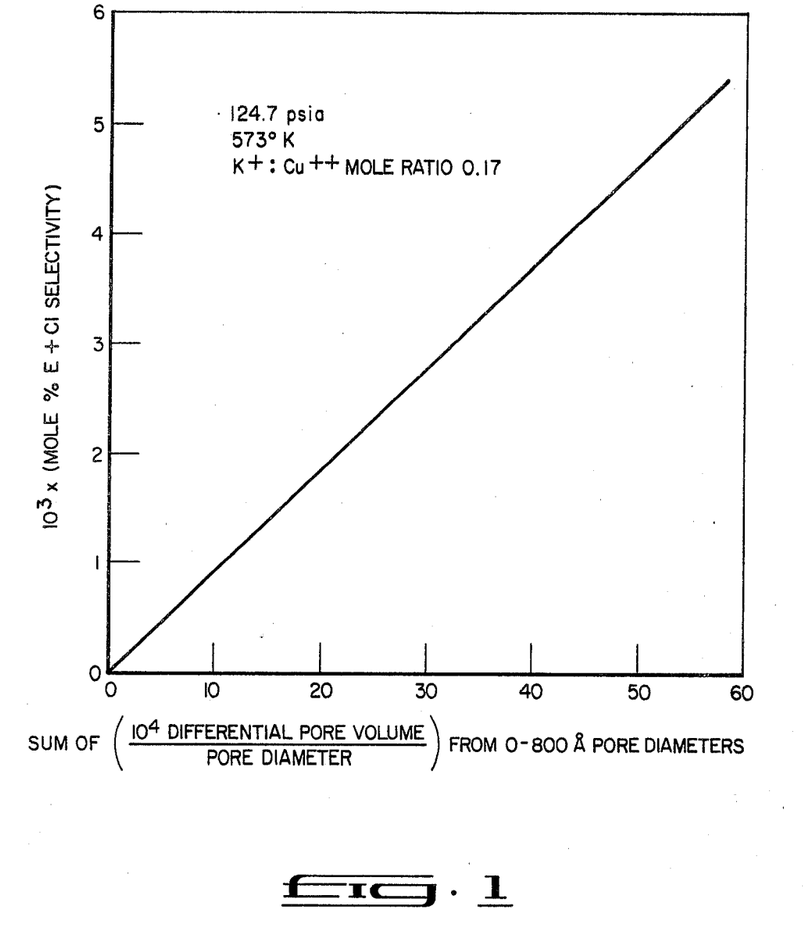
FIG. 1 shows the relationship of catalyst pore volume distribution to ethyl chloride selectivity.

The values of "sum of $\frac{10^4 \text{ differential pore volume}}{\text{pore diameter}}$"

in FIG. 1 were calculated using median diameters for each pore diameter range. For example, the value corresponding to the catalyst in Example 9 was calculated as follows:

$$\text{"Sum"} = \frac{10^4 \text{ cc}}{\text{g Å}} \left( \frac{0.0}{37.5} + \frac{0.0}{45} + \frac{0.0}{57.5} + \frac{0.0}{72.5} + \frac{0.0}{90} + \right.$$

$$\frac{0.001}{110} + \frac{0.0}{135} + \frac{0.042}{175} + \frac{0.091}{225} + \frac{0.157}{300} + \frac{0.005}{412.5} +$$

$$\left. \frac{0.008}{650} \right) = 12 \text{ cc/g·Å}$$

Corresponding values for Stauffer SCS206 (trademark of and sold by Stauffer Chemical Co.) and BASF 45% oxy catalysts (sold by BASF Chemical Co.) were 52 and 64 (average of 64.0 and 69.3) cc/gÅ, respectively.

The present invention provides a method for producing oxychlorination catalysts with essentially no porosity in pores having less than 150 Ångstroms, while maintaining the highest possible specific surface area.

In the present invention, surface area of only about 30 square meters per gram is sufficient for full initial fixed bed activity. However, it is of course desirable in terms of flexibility of production and increased lifetime to have as high a specific surface area as possible which is compatible with a high total porosity and micropores larger than 150 Ångstroms, and preferably less than 250 Ångstroms. Alumina catalyst carriers produced according to the instant invention inherently show higher specific surface areas in the 150 Å to 250 Å micropore diameters range than do alumina carriers produced by simple, conventional calcination.

While no actual experiments have been carried out, other non-basic oxychlorination catalyst supports such as bauxite, clays, silica, aluminosilicates and the like having a specific surface area larger than about 30 square meters per gram and having essentially no porosity in pores smaller than 150 Ångstroms will also afford copper chloride based oxychlorination catalysts the same advantage as the present invention, as will aluminas having these characteristics which are prepared by other methods.

Thus the instant invention provides reduced selectivity of catalysts to the tars components and lower boiling chlorinated ethylenes of current commercial processes. These components are believed to be the precursors to the catalyst coke. Catalyst coking in turn seriously shortens commercial catalyst lifetime with consequent loss of production during catalyst changes. In addition, loss of activity from covered or occluded copper chloride and excessive reactor pressure drop which increases from fracturing and dusting of the catalyst are likewise avoided. Thus the catalyst of the present invention will provide significantly increased lifetimes over commercial fixed bed ethylene oxychlorination catalysts, as well as reducing selectivity to ethyl chloride by-product at the expense of desired product ethylene dichloride.

The catalysts of the present invention require less potassium chloride or other Group I or II metal salts for superior ethylene dichloride selectivity than do conventional oxychlorination catalysts. Broad ranges of copper chloride in the catalysts of the present invention are from 6 to 20% by weight of the finished catalyst. Preferred range of copper chloride is from 9–16% by weight of the finished catalyst. The broad range of Group I or Group II metal salts such as potassium chloride is determined by potassium chloride to copper chloride mole ratio of from about 0.05 to about 1.0 respectively. The preferred range of potassium chloride is determined by a potassium chloride to copper chloride mole ratio of from about 0.05 to about 0.6. The catalysts of the present invention may be employed with inert diluents for temperature control in the same manner as the known catalysts of the prior art if desired. However, it is emphasized that temperature control for selectivity to ethylene dichloride as opposed to ethyl chloride is much less important with catalysts of the present invention than with conventional catalysts of the prior art.

The catalysts of the present invention are utilized under the same temperature and pressure conditions as are the catalysts of the prior art, except that such temperatures and pressures are less critical for selectivity to ethylene dichloride. Thus the present invention provides an improved ethylene oxychlorination catalyst comprising copper chloride, and mixtures of copper chloride and potassium chloride on an alumina support, the improvement comprising utilizing an alumina support having substantially no pores less than 150 angstroms in diameter and a surface area of at least 30 square meters per gram. The alumina support can be prepared by forming the alumina into the desired shape then placing the shaped alumina above liquid water in a closed vessel and heating for from about 2 to about 10 hours to a temperature of from about 150° C. to about 550° C. while allowing the pressure to reach autogeneous levels from steam in equilibrium with liquid water in a closed container, then recovering the alumina and calcining the recovered alumina for a period of time ranging from about 15 minutes to about 10 hours at a temperature of from about 450° C. to about 1000° C. Thereafter the final catalyst is prepared by placing catalytic salts on the alumina support, the most normal technique for such placing on the support comprises soaking said support for an effective length of time in an aqueous solution of copper chloride or mixtures of copper chloride and potassium chloride, and then drying the resulting catalyst prior to use.

The instant invention is more concretely described with reference to the examples below wherein all parts and percentages are by weight unless otherwise specified. The examples are provided to illustrate the present invention and not to limit it.

The particular carriers described in the examples of this invention were produced on a pelletizing disc using nitric acid as an agent to cause agglomeration of alumina powders into their final size and spherical shape. Other methods of agglomeration and shapes such as those produced by extrusion, tableting, and spray drying could also be used. Agents other than nitric acid to permit the agglomeration of the alumina powder may also be used.

EXAMPLE 1

The present invention is illustrated by the preparation of a catalyst from alumina powder. Alumina powder (Catalyst SB alumina, trademark of and sold by Conoco Chemical Co.) produced from the hydrolysis of aluminum alkoxides was spheroidized on a pelletizing disc (manufactured by Dravo Corp., Pittsburg, PA.) using typical operation practices as described in Perry's Handbook of Chemical Engineering, Chapter 8, pages 61–63, 5th Edition, McGraw-Hill. For bonding the powders into spheres, a 3% aqueous nitric acid solution was sprayed onto the powder rolling on the rotating pelletizing disc. The spherical product discharged from the pelletizing disc was approximately ¼ inch in diameter (3×5 U.S. standard mesh size). This product was dried overnight at 38° C.

One thousand (1000) grams of resulting spheres were placed in a one gallon autoclave with 5.6 moles of distilled water. The spheres were supported on a stainless steel screen to hold them above and out of the initial water layer. The autoclave was sealed and the contained materials were brought to a temperature of 260° C. for a period of 3 hours. The autoclave reached a pressure of 665 to 762 pounds per square inch gauge (psig). After this heating period the autoclave was allowed to cool to a temperature of approximately 110° C. at which point the autoclave was vented allowing the contained steam to escape. These spheres were then calcined for 3 hours at 1000° C.

A 500 milliliter (ml) sample of cooled spheres was soaked for 1 hour in a solution of 124.2 grams of $CuCl_2.2H_2O$ and 19.6 grams of KCl in 400 ml of distilled water. The liquid was decanted and the spheres were dried overnight at 127° C. The resulting oxychlorination catalyst contained 6.17% copper, 1.10% potassium, 6.7% chloride and 30.6% aluminum. The catalyst had a specific surface area of 56 square meters per gram and substantially all micropores in the 200 to 250 Ångstrom diameter range.

EXAMPLE 2

The second preparation of a catalyst of the present invention was carried out. A 500 ml sample of the autoclaved ¼ inch alumina spheres from Example 1 was soaked for 30 minutes in a solution of 37.7 grams of potassium chloride and 95.7 grams of $CuCl_2.2H_2O$ in 400 ml of distilled water. The liquid was decanted and the spheres were dried at 150° C. for 2 days. The resulting catalyst contained 4.25% copper, 2.12% potassium, 5.7% chloride and 29.1% aluminum. The catalyst had a specific surface area of 55 square meters per gram and substantially all of its micropores in the 200 to 250 Ångstrom diameter range.

EXAMPLE 3

Alumina spheres were prepared on a pelletizing disc and autoclaved at approximately 260° C. (exhibiting an autogenous pressure of 720 to 770 psig) as described in Example 1. These spheres were then calcined for 3 hours at 750° C. A 500 ml sample of these spheres was soaked for 1 hour in a solution of 124.2 grams $CuCl_2.2H_2O$ in 19.8 grams of KCl at 400 ml of distilled water. The liquid was decanted and the spheres were dried overnight at 250° F. The resulting oxychlorination catalyst contained 6.11% copper, 1.22% potassium, 6.7% chloride and 29% aluminum. The catalyst had specific surface area of 82 square meters per gram and had substantially all of its micropores in the 150–250 Ångstrom diameter range.

EXAMPLE 4

As a comparative example a 520 ml sample of 3×6 mesh alumina spheres (Houdry HSC-114 alumina, trademark of and sold by the Houdry Division of Air Products and Chemicals, Inc., Philadelphia, PA) preferred by Stauffer for the preparation of its commercial oxychlorination catalysts (U.S. Pat. No. 4,123,467) was soaked for 15 minutes in a solution of 206.0 grams of $CuCl_2.2H_2O$ and 54.0 grams of KCl and 400 ml of distilled water. The liquid was decanted and the spheres were dried overnight at 160° C. The resulting oxychlorination catalyst contained 6.45% copper, 2.22% potassium, 8.48% chloride and 31.2% aluminum by weight. The catalyst showed a specific surface area of 182 square meters per gram and the majority of its micropores in the 40 to 65 Ångstroms diameter range.

EXAMPLE 5

A comparison of the catalysts described in examples 1 through 4 was carried out. A 4-foot by 1-inch inside diameter nickel reactor was utilized. The feed gases were conducted to the top of the reactor through calibrated rotameters at a 110 psig head pressure. Conditions were chosen to similate operations in the first of a 3-reactor oxychlorination series. These reactors traditionally show greatest selectivity to by-products including coke. Under these conditions oxygen was a limiting reagent and thus percent oxygen conversion and the degree of peaking of the reactor thermal profile were direct measures of catalyst activity.

Timed ethylene dichloride (EDC) and water samples were obtained by emptying a pressurized glass knock-out vessel and analyzing the contents. The EDC samples were analyzed by gas liquid chromatography (GLC) in an FFAP ("free fatty acid phase") esterified polyethylene glycol column using a flame ionization detector. The test conditions are summarized in Table 1.

TABLE 1
CONDITIONS FOR TESTS OF CATALYSTS

| Catalysts | Gas Feed Rates, moles/hr | | | | % $O_2$ Conversion | Hourly Liquid Product Weight, g | |
|---|---|---|---|---|---|---|---|
| | $O_2$ | HCL | $C_2H_4$ | $N_2$ | | Crude EDC | Crude $H_2O$ |
| Example 1 | 2.4 | 11.8 | 12.7 | 107 | 98 | 333.0 | 111.9 |
| Example 2 | 2.4 | 11.8 | 12.7 | 107 | 62 | 228.5 | 71.4 |
| Example 3 | 2.4 | 11.8 | 12.7 | 107 | 98 | 338.8 | 118.6 |
| Example 4 | 2.4 | 11.8 | 12.7 | 107 | 96 | 320.0 | 111.1 |

Gas liquid chromatographic data on liquid ethylene dichloride for each catalyst test is set forth in Table 2. In Table 2 parenthetical values are retention times in seconds. The term "EtCl" represents ethyl chloride, while the term "trans" indicates trans-dichloroethylene. "Cis+tri" indicates the combined response from cis-dichloroethylene and trichloroethylene. "1,1,2-TCE" represents 1,1,2-trichloroethane and "2-ClEtOH" represents 2-chloroethanol "VCM" represents vinyl chloride monomer. All values are in area percent.

TABLE 2

| | GLC ANALYSES OF CRUDE EDC, AREA % | | | | | | | | | | |
|---|---|---|---|---|---|---|---|---|---|---|---|
| Catalyst | C2H4 | VCM | EtCl | trans | CCl4 | Cis + tri | CHCl3 | EDC | 1,1,2-TCE | Chloral | 2-ClEtOH |
| Example 1 | 0.4262 | 0.013 | 0.0751 | 0.0007 | 0.0373 | 0.0061 | 0.0075 | 99.2720 | 0.1562 | 0.0013 | 0.0000 |
| | (139) | (154) | (162) | (209) | (223) | (282) | (300) | (343) | (723) | (901) | |
| Example 2 | 0.3649 | 0.0000 | 0.0351 | 0.0006 | 0.0064 | 0.0014 | 0.0000 | 99.5335 | 0.0446 | 0.0000 | 0.0000 |
| | (141) | | (164) | (210) | (224) | (290) | | (349) | (727) | | |
| Example 3 | 0.4550 | 0.0137 | 0.0725 | 0.0007 | 0.0417 | 0.0063 | 0.0105 | 99.2066 | 0.1729 | 0.0121 | 0.0000 |
| | (140) | (155) | (163) | (209) | (244) | (283) | (301) | (345) | (725) | (905) | |
| Example 4 | 0.4125 | 0.0110 | 0.1336 | 0.0010 | 0.0294 | 0.0081 | 0.0321 | 99.1225 | 0.2106 | 0.0133 | 0.0000 |
| | (104) | (155) | (163) | (209) | (223) | (283) | (301) | (342) | (724) | (898) | |

EXAMPLE 6

Alumina spheres were formed, autoclaved, and calcined as described in Example 1. The alumina (4×6 mesh) prepared was utilized as the basic carrier for Examples 7 through 11.

EXAMPLE 7

A portion of the alumina of Example 6 (179.4 grams) was impregnated over a 15 minute period with 207 ml of a distilled water solution of 31.9 grams $CuCl_2.2H_2O$ and 19.60 grams KCl. Excess liquid was decanted and the spheres were dried overnight at 170° C. to yield 203.5 grams of catalyst.

EXAMPLE 8

A portion of the spheres of Example 6 (122.4 grams) was impregnated over a 15 minute period with 141 milliliters of a distilled water solution of 26.5 grams $CuCl_2.2H_2O$ and 26.6 grams KCl. Excess liquid was decanted and the spheres were dried overnight at 170° C. to yield 145.6 grams of catalyst.

EXAMPLE 9

A portion of the alumina of Example 6 (168.4 grams) was impregnated over a 15 minute period with 194 milliliters of a distilled water solution of 49.2 grams $CuCl_2.2H_2O$ and 13.0 grams KCl. Excess liquid was decanted and the spheres were dried for 2 days at 170° C.

EXAMPLE 10

A portion of the alumina prepared in Example 6 (123.5 grams) was impregnated over a 15 minute period with 142 milliliters of a distilled water solution of 25.7 grams $CuCl_2.2H_2O$ and 22.5 grams KCl. Excess liquid was decanted and the spheres were dried overnight at 170° C. to yield 144.0 grams of catalyst.

EXAMPLE 11

A portion of the Example 6 alumina (91.2 grams) was impregnated over a 15 minute period with 105 ml of a distilled water solution containing 27.7 grams $CuCl_2.2H_2O$ and 14.6 grams KCl. Excess liquid was decanted and the spheres were dried overnight at 170° C. to yield 109.3 grams of catalyst.

EXAMPLE 12

The catalysts produced in Example 7, 8, 9, 10, and 11 were loaded in two different configurations and tested as runs X and Y against commercial spherical catalysts tested as Run Z at a loading recommended by the Stauffer Chemical Company in U.S. Pat. No. 4,206,180 for use in the first of a three reactor series. Test conditions in such a reactor are summarized in Table 3. GLC analyses of the crude EDC liquid are summarized in Table 4. Catalyst loading patterns and thermal profiles are summarized in FIGS. 2, 3 and 4.

Figure 2:
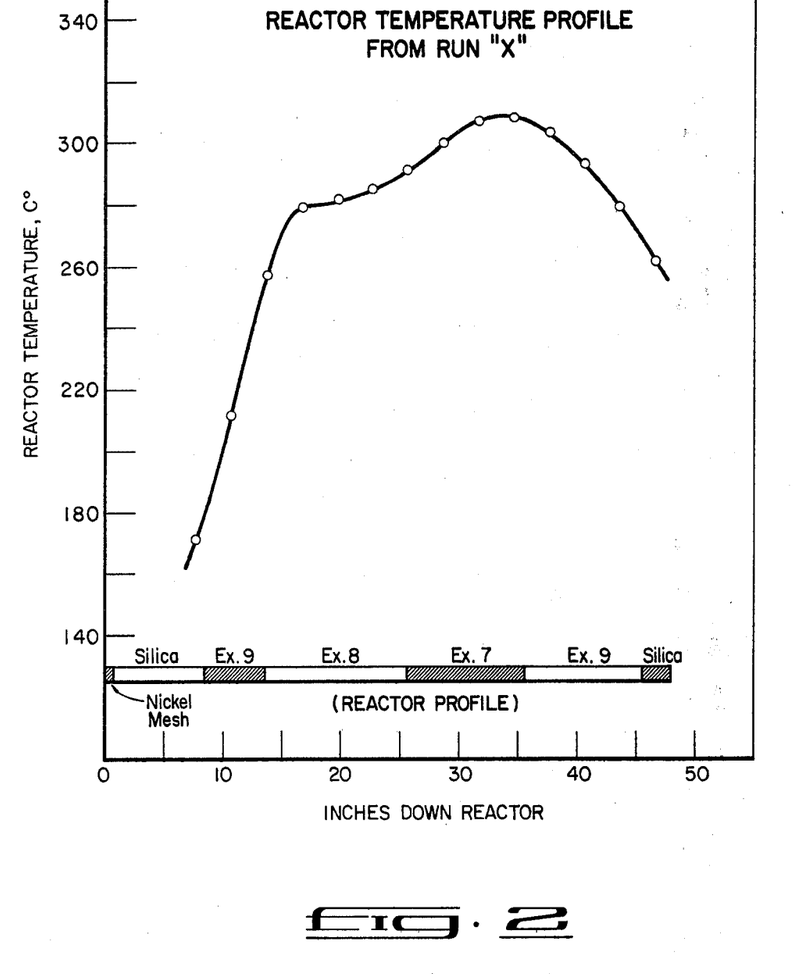
FIG. 2 shows the relationship of loading pattern with the catalysts of the present invention and the resulting reactor temperature profile.
Figure 3:
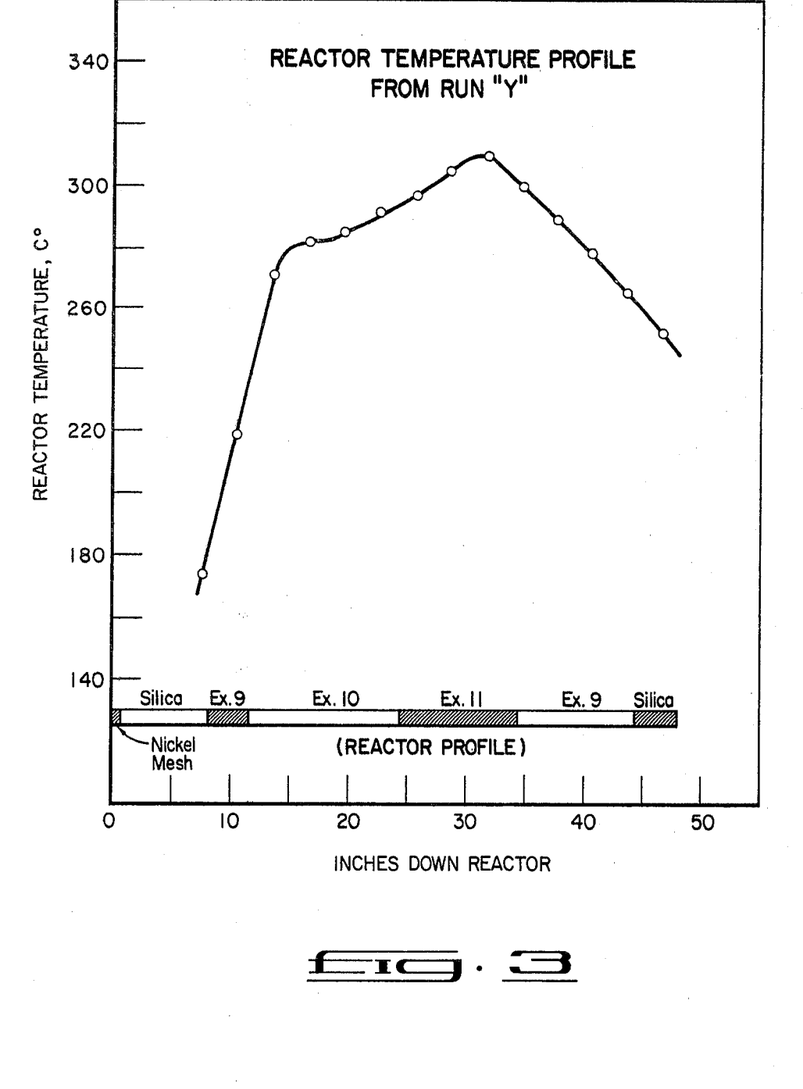
FIG. 3 shows the relationship of FIG. 2 with a second loading pattern.
Figure 4:
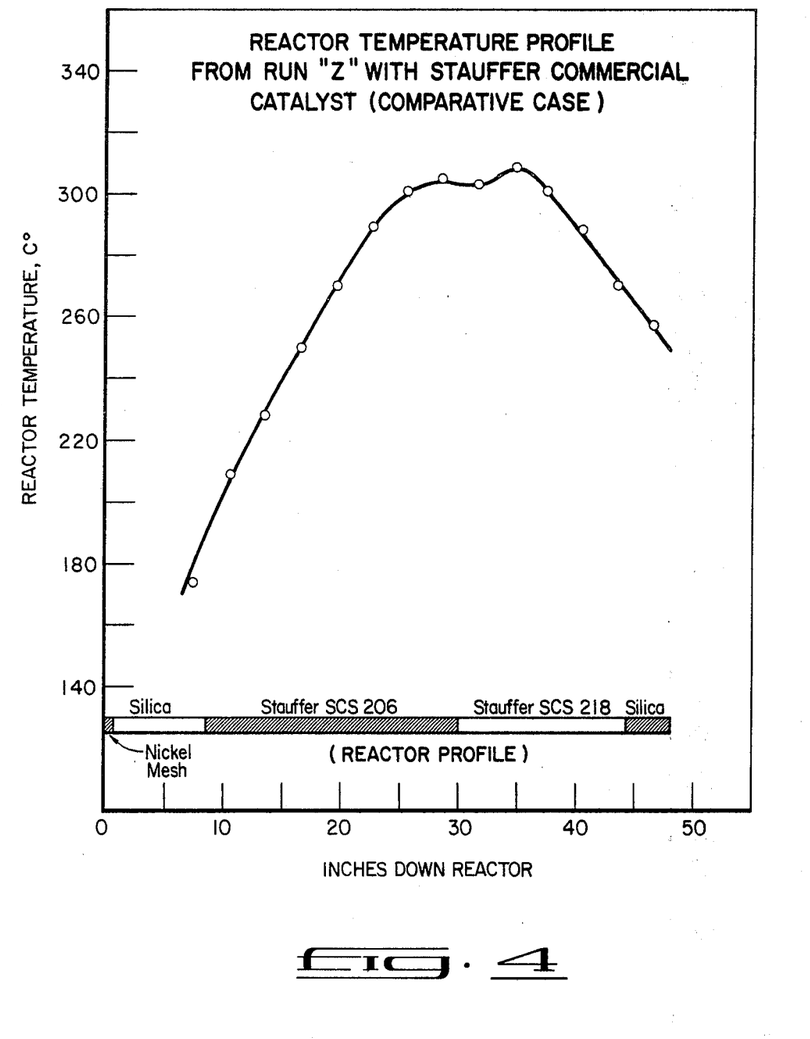
FIG. 4 shows the relationship of FIG. 2 in a comparison of a commercial catalyst with a catalyst of the present invention in a loading pattern and resulting reactor temperature profile.

An analysis of this data and the loading pattern indicates that regardless of the degree of loading and the order in which such materials are loaded into the reaction, the primary effect on the production of EDC occurs because of the structure of the carrier and not because of the various loadings on the catalyst. In addition, the temperature of the hot spot in the reactor tends to vary because of the particular pore diameter distribution of a supported catalyst.

TABLE 3

| | TEST CONDITIONS | | | | | | |
|---|---|---|---|---|---|---|---|
| Run | O2 | HCl | C2H4 | N2 | % O2 Conversion | Crude EDC | Crude H2O |
| X | 4.0 | 18.4 | 56.7 | 98 | 100 | 571.3 | 170.3 |
| Y | 4.0 | 18.4 | 56.7 | 98 | 100 | 578.9 | 152.8 |
| Z | 4.0 | 18.4 | 56.7 | 98 | 97 | 518.0 | 170.1 |

Table 4 shows the gas chromatographic analysis of the crude EDC in area percent. In Table 4 all abbreviations and symbols are the same as for Table 3.

TABLE 4

| | GLC ANALYSES OF CRUDE EDC, AREA % | | | | | | | | | | |
|---|---|---|---|---|---|---|---|---|---|---|---|
| Run | C2H4 | VCM | EtCl | trans | CCl4 | Cis + tri | CHCl3 | EDC | 1,1,2-TCE | Chloral | 2-ClEtOH |
| X | 1.1770 | 0.0112 | 0.0718 | 0.2004 | 0.0321 | 0.1465 | 0.0163 | 98.2947 | 0.0327 | 0.0000 | 0.0000 |
| | (138) | (153) | (161) | (207) | (207) | (220) | (287) | (339) | (715) | | |
| Y | 0.9515 | 0.0122 | 0.0919 | 0.2203 | 0.0836 | 0.1557 | 0.0082 | 98.4182 | 0.0374 | 0.0000 | 0.0000 |
| | (138) | (153) | (161) | (207) | (220) | (287) | | (339) | (716) | | |
| Z | 1.1572 | 0.0435 | 0.8274 | 0.1656 | 0.0271 | 0.2274 | 0.0120 | 97.4621 | 0.0337 | 0.0000 | 0.0000 |
| | (138) | | (161) | (207) | (220) | (287) | | (340) | (714) | | |
| Z | 0.8481 | 0.0820 | 0.7379 | 0.1665 | 0.0268 | 0.2045 | 0.0227 | 97.8479 | 0.0289 | 0.0000 | 0.0000 |
| | (137) | | (160) | (206) | (219) | (286) | | (339) | (713) | | |

The pore volume distributions of various catalysts previously illustrated are set forth in Table 5.

TABLE 5

SPECIFIC SURFACE AREAS AND PORE VOLUME DISTRIBUTIONS

| | Example 1 | 2 | 3 | 4 | 7 | 8 | 9 | 10 | 11 | 12 |
|---|---|---|---|---|---|---|---|---|---|---|
| Form of material analyzed | ¼" spheres | ¼" spheres | ¼" spheres | 3–6 mesh spheres | 4–6 mesh spheres | 4–6 mesh spheres | 4–6 mesh spheres | 4–6 mesh spheres | 4–6 mesh spheres | 4–6 mesh spheres |
| Specific surface Area, m²/g | 56 | 55 | 82 | 182 | 64 | 52 | 58 | 53 | 48 | 221 |
| Differential Pore Volume (cc/g) for the Following Pore Diameters (Å) | | | | | | | | | | |
| 35–40 | 0.0 | 0.0 | 0.0 | 0.006 | 0.0 | 0.0 | 0.0 | 0.0 | 0.0 | 0.023 |
| 40–50 | 0.0 | 0.0 | 0.0 | 0.035 | 0.0 | 0.0 | 0.0 | 0.0 | 0.0 | 0.037 |
| 50–65 | 0.002 | 0.0 | 0.001 | 0.057 | 0.0 | 0.0 | 0.0 | 0.001 | 0.004 | 0.130 |
| 65–80 | 0.0 | 0.001 | 0.002 | 0.018 | 0.0 | 0.0 | 0.0 | 0.003 | 0.0 | 0.070 |
| 80–100 | 0.003 | 0.0 | 0.0 | 0.020 | 0.0 | 0.0 | 0.0 | 0.002 | 0.005 | 0.034 |
| 100–120 | 0.001 | 0.0 | 0.009 | 0.016 | 0.002 | 0.0 | 0.001 | 0.0 | 0.005 | 0.011 |
| 120–150 | 0.003 | 0.007 | 0.026 | 0.014 | 0.004 | 0.0 | 0.0 | 0.005 | 0.001 | 0.017 |
| 150–200 | 0.031 | 0.060 | 0.153 | 0.016 | 0.072 | 0.052 | 0.042 | 0.023 | 0.033 | 0.005 |
| 200–250 | 0.172 | 0.141 | 0.074 | 0.011 | 0.171 | 0.149 | 0.091 | 0.170 | 0.208 | 0.007 |
| 250–350 | 0.066 | 0.059 | 0.040 | 0.011 | 0.074 | 0.074 | 0.157 | 0.096 | 0.025 | 0.009 |
| 350–500 | 0.007 | 0.007 | 0.007 | 0.006 | 0.011 | 0.002 | 0.005 | 0.006 | 0.002 | 0.010 |
| 500–800 | 0.004 | 0.001 | 0.0 | 0.001 | 0.005 | 0.0 | 0.008 | 0.006 | 0.008 | 0.010 |
| 800–1,000 | 0.0 | 0.0 | 0.0 | 0.015 | 0.0 | 0.0 | 0.0 | 0.0 | 0.0 | 0.006 |
| 1,000–250,000 | 0.230 | 0.239 | 0.236 | 0.134 | 0.180 | 0.188 | 0.225 | 0.155 | 0.153 | 0.106 |
| Total Pore Volume, cc/g | 0.520 | 0.516 | 0.548 | 0.358 | 0.521 | 0.465 | 0.530 | 0.466 | 0.443 | 0.474 |

Figure 5:
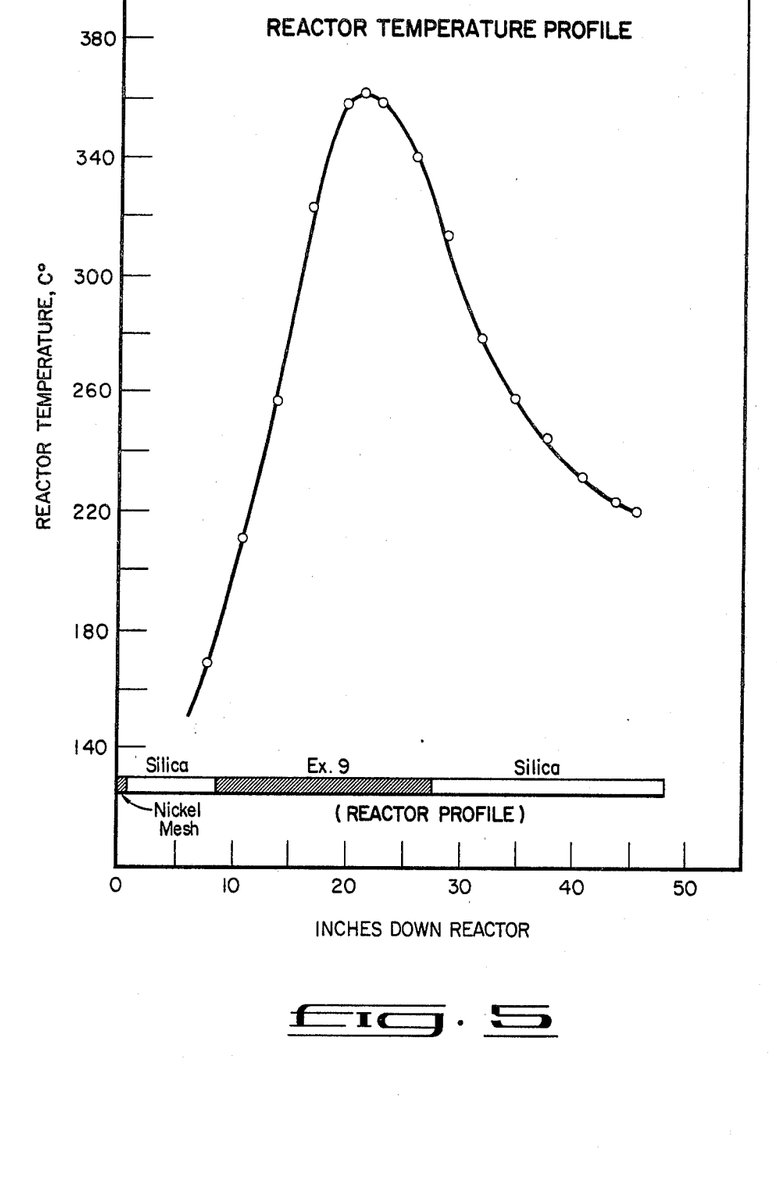
FIG. 5 shows an unoptimized loading pattern for a catalyst of the invention and resulting reactor temperature profile.

Comparative runs were carried out as described in Example 12 using the catalyst of Example 9. The reaction hot spot shown in FIG. 5 illustrates that excellent results can be obtained even when extremely undesirable conditions are maintained. FIG. 5 shows that a temperature of over 360° C. was reached, which is acknowledged as too hot for good performance with ethylene oxychlorination catalysts in the art. However, when this catalyst was compared to catalysts made from commercially used γ-alumina carrier (Houdry HSC-114) as set forth in FIG. 6, it can be seen that the support of the present invention provides reduced ethyl chloride selectivities (and increased EDC selectivities) much less sensitive to temperature variations than with the standard commercial catalysts.

Figure 6:
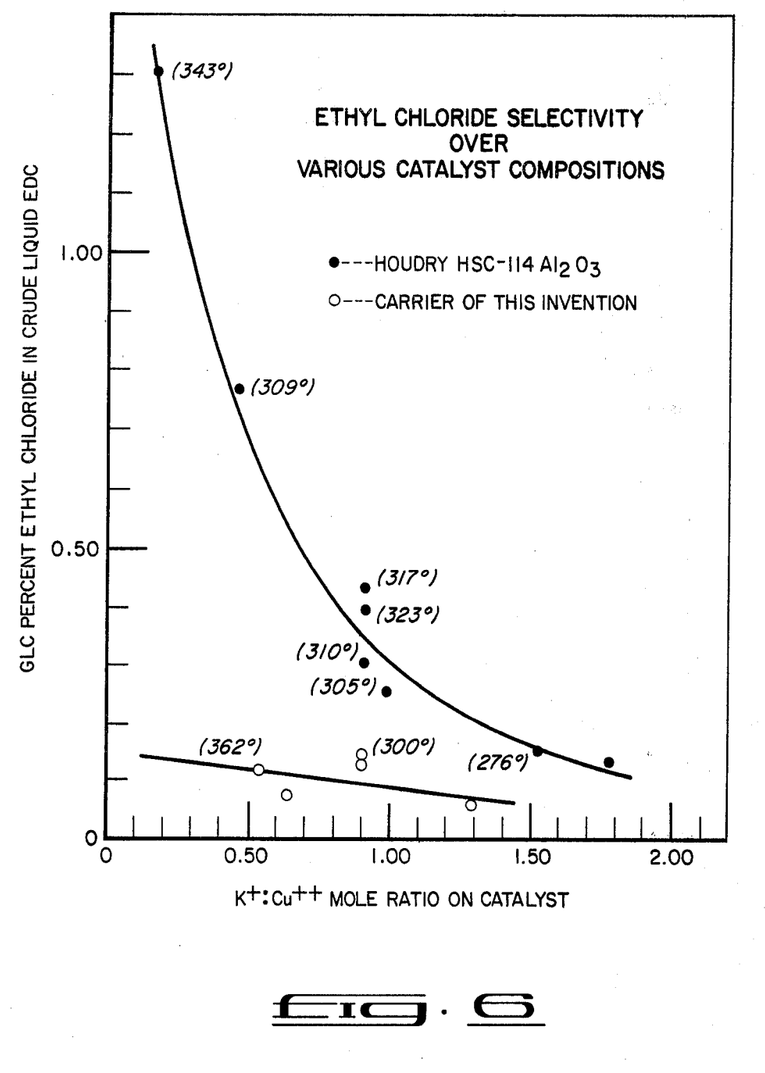
FIG. 6 shows a comparison of the combined effects of temperature of $K^+:Cu^{++}$ mole ratio on ethyl chloride selectivity for catalyst prepared from alumina and the supports of the present invention.

FIG. 6 shows the combined effects of temperature and $K^+:Cu^{++}$ mole ratio on the selectivity to ethyl chloride of oxy catalysts made from the usual γ-alumina and the supports of this invention, tested under the conditions of Example 12. In FIG. 6, the legend "carrier of this invention" generally fits the curve generated by each of the catalysts produced in Examples 7, 8, 9, 10, and 11.

While certain embodiments and details have been shown for the purpose of illustrating this invention, it will be apparent to those skilled in this art that various changes and modifications may be made herein without departing from the spirit or scope of the invention.

We claim:

1. A method for preparing ethylene oxychlorination catalysts comprising impregnating an alumina carrier with copper chloride or mixtures of copper chloride and Group I and Group II metal chlorides, wherein the alumina carrier has substantially no pores less than 150 Ångstroms in diameter and a specific surface area of at least 30 square meters per gram.

2. A method as described in claim 1 wherein the alumina carrier is prepared by
   (a) forming the alumina into the desired shape;
   (b) placing the alumina above liquid water in a closed vessel and heating for from about 2 to about 10 hours to a temperature of from about 150°–550° C., while allowing pressure to reach autogeneous levels from steam in equilibrium with liquid water, then
   (c) recovering the alumina and calcining the recovered alumina for from 15 minutes to about 10 hours at a temperature of from about 450° C. to about 1000° C.

3. A method as described in claim 2 wherein the Group I and Group II metal chlorides are selected from the group consisting of sodium chloride and potassium chloride.

4. A method as described in claim 2 wherein the copper chloride or mixtures of copper chloride and potassium chloride or copper chloride and sodium chloride are placed on the alumina support by soaking said support for an effective length of time in an aqueous solution of copper chloride or mixtures of copper chloride and potassium chloride or copper chloride and sodium chloride and the resulting catalyst dried prior to use.

5. An ethylene oxychlorination catalyst comprising copper chloride or mixtures of copper chloride and Group I or Group II halides on an alumina carrier having substantially no pores less than 150 Ångstroms in diameter, and a specific surface area of at least 30 square meters per gram, wherein the catalyst is prepared by a process comprising
   (a) forming the alumina into the desired shape;
   placing the alumina above liquid water in a closed vessel and heating for from about 2 to about 10 hours to a temperature of from about 150° C. to about 550° C., while allowing the pressure to reach autogeneous levels from steam in equilibrium with liquid water, then
   (c) recovering the alumina and calcining for from about 15 minutes to about 10 hours at a temperature of from about 450° C. to about 1000° C., then,
   (d) placing the alumina support in a solution of potassium chloride, copper chloride and mixtures of these for an effective length of time, then
   (e) recovering the alumina containing impregnated copper chloride, potassium chloride or mixtures of these and drying.

* * * * *

UNITED STATES PATENT AND TRADEMARK OFFICE
CERTIFICATE OF CORRECTION

PATENT NO. : 4,414,136
DATED : November 8, 1983
INVENTOR(S) : Ronald J. Convers and Richard K. Oberlander It is certified that error appears in the above-identified patent and that said Letters Patent are hereby corrected as shown below:

First page of patent where it states Inventor,
  --Richard K. Oberlander, Ponca City, Oklahoma--
  should be inserted after Ronald J. Convers, Ponca City, Oklahoma.

Column 2, line 9, "3,202,4880" should be --3,202,480--.

Signed and Sealed this

Twenty-fourth Day of January 1984

[SEAL]

Attest:

GERALD J. MOSSINGHOFF

*Attesting Officer*    *Commissioner of Patents and Trademarks*